United States Patent [19]

Burson

[11] Patent Number: 4,517,368
[45] Date of Patent: May 14, 1985

[54] 2,3-DICHLORO-5-IODOPYRIDINE AND METHODS OF MAKING AND USING THE SAME

[75] Inventor: Richard L. Burson, Midland, Mich.
[73] Assignee: The Dow Chemical Company, Midland, Mich.
[21] Appl. No.: 529,200
[22] Filed: Sep. 6, 1983
[51] Int. Cl.$^3$ .................................... C07D 213/61
[52] U.S. Cl. ................................ 546/303; 546/345
[58] Field of Search ...................... 546/345, 292, 303
[56] References Cited

U.S. PATENT DOCUMENTS 4,046,553  9/1977  Takahashi et al. ............... 546/345
4,327,216  4/1982  Martin ............................ 546/345

FOREIGN PATENT DOCUMENTS 0021613  7/1981  European Pat. Off. ........... 546/345
1599121  9/1981  United Kingdom ............... 546/345
1599122  9/1981  United Kingdom ............... 546/345

OTHER PUBLICATIONS

Gribble et al., Tetrahedron Letters, vol. 21, pp. 4137–4140.

Primary Examiner—Joseph Paul Brust

[57] ABSTRACT

The novel compound 2,3-dichloro-5-iodopyridine is prepared by chlorinating 3-chloro-5-iodo-2-pyridinol or by lithiating 2-bromo-2,3-dichloropyridine at a reduced temperature and thereafter iodinating the thus produced lithiopyridine. The compound 2,3-dichloro-5-iodopyridine is useful as a chemical intermediate in the preparation of pyridyloxyphenoxypropionic acids, and esters and amides thereof, which are valuable herbicides. The 2,3-dichloro-5-lithiopyridine and 3-chloro-5-iodo-2-pyridinol intermediates are also novel.

20 Claims, No Drawings

2,3-DICHLORO-5-IODOPYRIDINE AND METHODS OF MAKING AND USING THE SAME

BACKGROUND OF INVENTION

The present invention relates to the novel compound 2,3-dichloro-5-iodopyridine and to methods of making it. The present invention also relates to 2,3-dichloro-5-lithiopyridine and 3-chloro-5-iodo-2-pyridinol, which are novel intermediates used in preparing 2,3-dichloro-5-iodopyridine, and to the methods of preparing these intermediates.

Japanese Patent Application No. Sho-52-86636 discloses 2-(4-(5-iodo-2-pyridyloxy)phenoxy)propionic acid compounds and derivatives thereof which are used in the preparation of 2-(4-(5-trifluoromethyl-2-pyridyloxy)phenoxy)propionic acid and derivatives which are valuable herbicides. No methods of preparing the iodopyridyloxyphenoxypropionates are disclosed.

British Patent Specification No. 1,599,121 discloses methyl α-[4-(3-chloro-5-iodo-2-pyridyloxy)phenoxy]-propionate (page 14, lines 14 and 15) but does not teach how to make this compound.

Heretofore, 2,3-dichloro-5-iodopyridine has not been disclosed. Initial attempts to prepare 2,3-dichloro-5-iodopyridine employing standard iodinating techniques by iodinating the reactive 5-position of 2-aminopyridine or 2-pyridinol and thereafter chlorinating the 3-position failed to produce this compound. It was not until the methods described herein were employed, that 2,3-dichloro-5-iodopyridine was produced.

SUMMARY OF THE INVENTION

Briefly, in accordance with the present invention, 2,3-dichloro-5-iodopyridine is prepared by lithiating 5-bromo-2,3-dichloropyridine at a reduced temperature to form 2,3-dichloro-5-lithiopyridine. The 2,3-dichloro-5-lithiopyridine is then reacted with $I_2$ at a reduced temperature to form 2,3-dichloro-5-iodopyridine. The resulting product is then extracted and recovered. 2,3-Dichloro-5-iodopyridine is in the form of a white solid and has a melting point of from 56.5° C. to 57.5° C.

A second method of preparing 2,3-dichloro-5-iodopyridine involves the iodination of 5-chloro-6-hydroxynicotinic acid with $I_2$ in an aqueous alkaline iodide solution resulting in 3-chloro-5-iodo-2-pyridinol. 3-Chloro-5-iodo-2-pyridinol is then reacted with a chlorinating agent whereby 2,3-dichloro-5-iodopyridine is formed.

2,3-Dichloro-5-iodopyridine is useful as a chemical intermediate in the preparation of 2-(4-(3-chloro-5-iodopyridyloxy)phenoxy)propionic acid and esters, salts and amides thereof which are herbicides and which are also used in the preparation of 2-(4-(3-chloro-5-trifluoromethylpyridyloxy)phenoxy)propionic acid and derivatives thereof, as taught in U.K. Patent Specification No. 1,599,121, which are also herbicides.

DETAILED DESCRIPTION OF THE INVENTION

In practicing the present invention, 5-bromo-2,3-dichloropyridine is lithiated by reacting it with a lithiating agent, such as, n-butyl lithium or lithium diisopropylamide, in an inert carrier medium, such as, tetrahydrofuran, dry ethyl ether or other etherial solvents, at a reduced temperature of about −70° C. or lower. This lithiation reaction results in the formation, in situ, of 2,3-dichloro-5-lithiopyridine, a novel intermediate which is transitory and non-isolatable but is within the scope of the present invention. After the lithiation reaction is complete, usually in from about 5 to about 60 minutes, iodine ($I_2$) is added to the reaction mixture whereby 2,3-dichloro-5-iodopyridine is formed. The iodine addition is also conducted at a reduced temperature of about −70° C. or lower and the iodination reaction is also usually complete in from about 5 to about 60 minutes.

The amount of inert carrier medium is not critical but it is advantgeous to employ enough inert carrier medium to keep the 5-bromo-2,3-dichloropyridine in solution at reaction temperatures, generally from about 10 to about 20 parts by weight inert carrier medium per part by weight pyridine starting material. The relative proportions of reactants to be employed is not critical because some of the product will be formed when employing and proportions of reactants. The reaction consumes the reactants, however, in the ratio of one mole of 5-bromo-2,3-dichloropyridine per mole of lithium and iodine. It is preferred to use an excess molar amount of lithium and iodine so that the 5-bromo-2,3-dichloropyridine starting material and 2,3-dichloro-5-lithiopyridine intermediate are completely consumed.

In carrying out the present reaction, neither the rate of addition nor the order of addition of the reactants is critical. Usually, the 5-bromo-2,3-dichloropyridine and the inert carrier medium are added to an appropriate reaction vessel and cooled to a temperature less than about −70° C. and preferably less than or equal to about −78° C. The lithiating agent, preferably n-butyl lithium, is then added slowly to the reaction mixture. The $I_2$ is then added, preferably immediately after formation of 2,3-dichloro-5-lithiopyridine because of the relatively unstable nature of the lithiopyridine intermediate, to the reaction mixture resulting in the formation of 2,3-dichloro-5-iodopyridine.

The present reaction is typically conducted in the presence of mild agitation sufficient to maintain an essentially uniform dispersion of the reactants in the carrier medium. Ambient pressures are advantageously employed although not critical.

After completion of the reaction, the desired product is recovered and isolated employing standard separatory and purification techniques, such as solvent extraction and recrystallization.

The following chemical equation characterizes the present reaction:

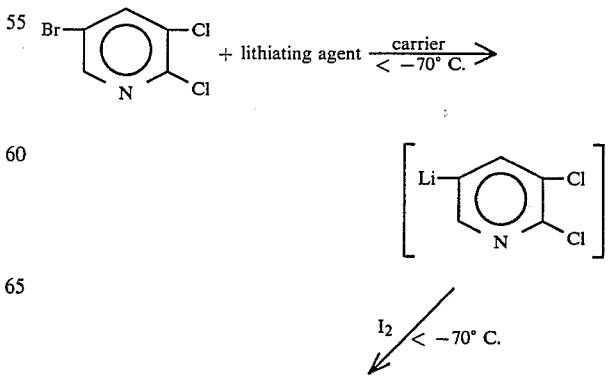

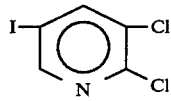

No attempt has been made to balance the above equation.

Alternatively, the present compound is prepared by reacting 5-chloro-6-hydroxynicotinic acid with I₂ in an aqueous alkaline iodide solution to form 3-chloro-5-iodo-2-pyridinol. This reaction is conveniently conducted at an elevated temperature of between 40° C. and 150° C. and preferably at about 100° C. Lowering the pH of the reaction mixture to ≦1 such as, for example, by addition to the reaction mixture of SO₂, will precipitate the 3-chloro-5-iodo-2-pyridinol from the reaction mixture.

The 3-chloro-5-iodo-2-pyridinol is reacted with a suitable chlorinating agent, such as, Cl₂, COCl₂ (phosgene), PCl₅, POCl₃, thionyl chloride (SOCl₂) or mixtures thereof, at an elevated temperature, preferably at reflux. The reaction mixture is then poured into cold water or crushed ice and the resulting precipitate isolated by filtration. The product, i.e., 2,3-dichloro-5-iodo-pyridine, may then be further purified employing standard purification and isolation techniques, such as, for example, solvent extraction and recrystallization.

This alternate method of preparing the present compound can be characterized as follows:

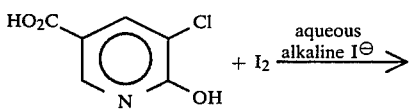

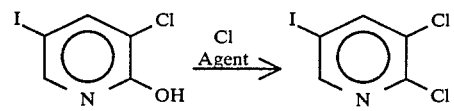

No attempt has been made to balance the above equation.

In one embodiment of the present invention, 5-bromo-2,3-dichloropyridine is dissolved in ethyl ether and cooled to about −78° C. A slight excess molar quantity of n-butyl lithium, dissolved in hexane, is slowly added to the reaction mixture with mild agitation. After about 0.5 hour of stirring, a slight excess molar quantity of I₂, dissolved in ethyl ether, is added to reaction mixture with mild agitation. After about 0.5 hour of stirring, the reaction mixture is allowed to warm to room temperature and the 2,3-dichloro-5-iodopyridine is isolated employing standard separatory and purification techniques.

In a preferred embodiment of the present invention, 3-chloro-5-iodo-2-pyridinol is reacted with an effective amount of a PCl₅/POCl₃ mixture at reflux until 2,3-dichloro-5-iodopyridine is formed, usually from about ½ to about 24 hours. The reaction mixture is then poured into crushed ice resulting in the precipitation of the desired product, i.e., 2,3-dichloro-5-iodopyridine, which is isolated and purified.

The following examples represent the practice of the present invention but should not be construed as limiting its scope. No attempt has been made to balance any chemical equation described herein.

EXAMPLE 1

Preparation of 2,3-dichloro-5-iodopyridine

STEP A

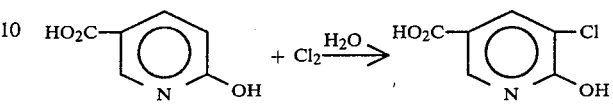

A one liter (1 l) 3-necked round bottom flask, fitted with a mechanical stirrer, a gas sparge tube, and a dry ice/acetone condenser with a drying tube, was charged with 75.0 grams (g) (0.539 mole) of 6-hydroxynicotinic acid (obtained from Aldrich Chemical Company) and 500 milliliters (ml) of deionized water. Chlorine (45.88 g; 0.647 mole) was bubbled into the reaction over a 1.5 hour period while the temperature was kept <25° C. The resulting tan slurry was stirred for 2 hours at room temperature. A tan solid was isolated by vacuum filtration, washed with 50–100 ml of deionized water and air dried. The tan solid was further dried by placing the solid in a one liter 3-necked round bottom flask, equipped with a mechanical stirrer, a thermometer with a temperature controller, a Dean-Stark trap with a condenser and a heating mantle, and azeotropically distilling the water with toluene (~700 ml charged initially). The resulting mixture was cooled to room temperature and the tan solid was isolated by filtration. After drying overnight under aspirator vacuum at 50° C., 77.0 g (82–83% of theoretical) of solid was obtained.

STEP B

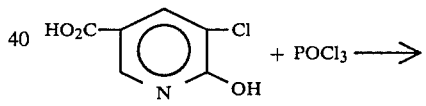

A 250 ml 3-necked round bottom flask with a thermowell was equipped with a mechanical stirrer, a dropping funnel and a condenser topped with a N₂ inlet and charged with 34.0 g (0.196 mole) of 5-chloro-6-hydroxynicotinic acid, from Step A, and 40 ml (67.0 g; 0.437 mole of phosphorus oxychloride) (POCl₃). The resulting tan slurry was heated to 105° C. where the liquid refluxed briefly. Within 15 minutes, the tan solid dissolved resulting in a black solution and the refluxing ceased. The reaction mixture was stirred and heated under N₂ at 105° C. for 2.5 hours. After the solution had cooled to room temperature, the black liquid was poured into a 2 liter 3-necked round bottom flask, fitted with a mechanical stirrer and a condenser, and charged with ice. The original reaction vessel was rinsed with water and the contents added to the second vessel. The reaction mixture was stirred overnight at ambient temperature. A solid was isolated by vacuum filtration, washed with water and air dried. The solid was transferred to a 2 liter 3-necked round bottom flask fitted with a mechanical stirrer, a thermometer and a Dean-Stark trap topped with a condenser with a N₂ inlet. A small amount of acetone was used to rinse the funnel and was added to the flask together with about one (1) liter of toluene. The acetone and residual water was removed by distillation. The mixture was filtered while hot to remove a small amount of black solid and gave a clear brown liquid. The brown liquid (toluene solution) was cooled to give 23.1 g of crude product (tan solid) having a melting point of 150°–156° C. Evaporation of the toluene produced an additional 12.12 g of tan solid.

STEP C

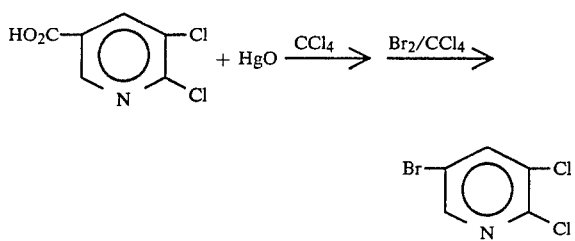

An oven dried, 250 ml 3-necked round bottom flask, equipped with a reflux condenser topped with an N₂ inlet, an addition funnel, a mechanical stirrer and a thermometer with a temperature controller, was flushed with N₂ and charged with 12.0 g (0.0625 mole) of 5,6-dichloronicotinic acid (from Step B), 17.45 g of (0.0806 mole) of red mercuric oxide and 100 ml of CCl₄. The reaction mixture (a red-orange slurry) was stirred under N₂ at reflux, using two 175 watt infrared heat lamps as the heat source, for 2 hours. A solution of 12 g (0.075 mole) of Br₂ in 25 ml of CCl₄ was added to the refluxing reaction mixture over a 5 hour period. The reaction mixture was stirred under N₂ at reflux overnight. In the morning, with most of the deep red color dissipated, 40 ml of saturated NaHCO₃ solution was added to the cooled reaction mixture. The reaction mixture was stirred for one hour at ambient temperature and filtered through a Celite pad. The resulting precipitate was thoroughly washed with methylene chloride. The combined organic layers were washed with water (2×100 ml) and 100 ml of saturated NaCl solution, dried over anhydrous MgSO₄, filtered and evaporated to dryness. The residual light brown oil was taken up in pentane, filtered and evaporated to dryness reslting in 10.35 g of a tan oil that was 89.5% pure as indicated by the area percent on a capillary gas chromatograph (gc) (0.5 μl of neat oil) employing standard gas chromatography (gc) procedures. The tan oil was transferred to a 50 ml miniware flask and was distilled through a short path distillation head. Only one fraction was observed that had a boiling point of 55°–65° C. @ ~1 torr. The oil, which was ~95 percent pure as indicated by gc, crystallized to a white solid which had a melting point of 30.0°–31.0° C.

STEP D

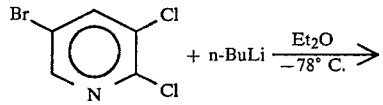

-continued
STEP D

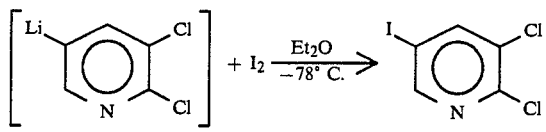

All glassware used in Step D was dried in an oven at 100° C. overnight and cooled to room temperature under N₂ prior to use. A 250 ml 3-necked round bottom flask, equipped with a magnetic stirrer, a thermometer, a septum, and an additional funnel topped with an N₂ inlet, was charged with 5.7 g (25 mmol) of 5-bromo-2,3-dichloropyridine (from Step C) and 125 ml of ethyl ether freshly distilled from sodium-benzophenone ketyl. The reaction mixture was cooled to −78° C. and 16.1 ml of ~1.6M n-butyl lithium in hexane was slowly added to the reaction mixture from a dried syringe. Little or no exotherm was noted although the reaction mixture immediately turned brown. The reaction mixture was stirred for 0.5 hour at −78° C. and then 7.61 g (30 mmol) of I₂ in ~30 ml of freshly distilled ether was slowly added so that the temperature was maintained less than −70° C. The reaction mixture was stirred for 0.5 hour at −78° C. and then allowed to warm to room temperature. The reaction mixture was poured into water and the layers were separated. The organic layer was washed with 50 ml of 1.0N sodium thiosulfate, 50 ml of water and 50 ml of saturated NaCl solution. The organic layer was dried over anhydrous MgSO₄, filtered and evaporated to dryness to give a brown oil. The oil was taken up in pentane, filtered through glass wool and evaporated to dryness resulting in 5.7 g of a brown oil that upon standing partially crystallized to needles. The mixture of oil and needles was warmed to give a homogeneous solution. The neat oil was analyzed by capillary gc and showed one major product (~80% by area) with a longer retention than the starting material. The oil was taken up in methanol and recrystallized to give 2.05 g of a white solid having a melting point of 56.5° C.–57.5° C. The structure of the product being 2,3-dichloro-5-iodopyridine was confirmed by nuclear magnetic resonance spectra (NMR) and mass spectroscopy.

EXAMPLE 2

Preparation of 2,3-Dichloro-5-iodopyridine

STEP 1

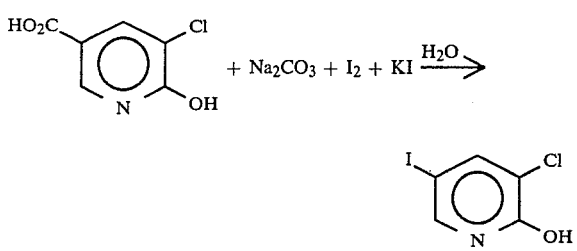

A 250 ml 3-necked round bottom flask, fitted with a reflux condenser, thermometer, addition funnel and magnetic stirrer, was charged with 3.47 g (0.02 mole) of 5-chloro-6-hydroxynicotinic acid (from Example 1, STEP A) and 8.6 g (0.03 mole) of sodium carbonate in 90 ml of water. The reaction mixture was stirred and heated to 100° C. under N₂. A solution of 5.1 g (0.02 mole) of iodine and 5.1 g (0.03 mole) of KI in 35 ml of water was added to the reaction mixture over 0.5 hour to minimize foaming. The reaction mixture was stirred for 1 hour at 100° C. The mixture was cooled to room temperature and the addition funnel was replaced with a gas sparge tube. SO₂ was passed through the mixture causing the formation of a tan precipitate. The SO₂ addition was maintained until the pH was <1. The slurry was stirred for 1 hour. The precipitate was isolated by filtration, washed with water and air dried resulting in 4.05 g of a tan solid having a melting point of 202°–209° C.

STEP 2

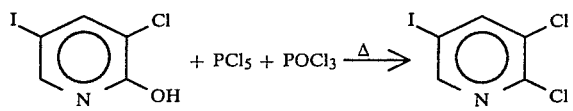

A 50 ml 3-necked round bottom flask, equipped with a thermometer, a reflux condenser topped with a N₂ inlet, a stopper and a magnetic stirrer, was charged with 3.50 g (0.0137 mole) of 3-chloro-5-iodo-2-pyridinol, from STEP 1 above, 3.00 g (0.0144 mole) of phosphorus pentachloride and 5–10 ml of phosphorus oxychloride. The reaction mixture was heated to reflux and the solid dissolved resulting in a golden brown solution. The reaction mixture was stirred under N₂ at reflux for 4 hours and then cooled to room temperature. The reaction mixture was poured into crushed ice and allowed to stand for about 1 hour. A tan precipitate, which was shown to be product and unreacted starting material, formed and was isolated by filtration and washed with pentane. The aqueous layer was also washed with pentane. The combined organic layers were washed with deionized water and saturated NaCl, dried over anhydrous MgSO₄, filtered and evaporated to dryness to give 0.4 g of a dark oil that crystallized upon standing.

EXAMPLE 3

Preparation of 2,3-Dichloro-5-iodopyridine

STEP 1

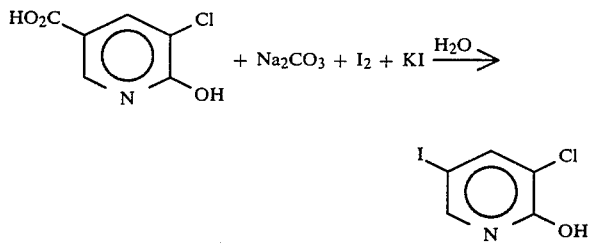

Substantially the same procedures described in STEP 1 of Example 2 were employed using 12.6 g (72.6 mmoles) of 5-chloro-6-hydroxynicotinic acid, 12.83 g (121 mmoles) of Na₂CO₃, 20.47 g (80.7 mmoles) of I₂, 20.09 g (121 mmoles) of KI and 500 ml of H₂O. The reaction produced 17.2 g of a tan solid.

STEP 2

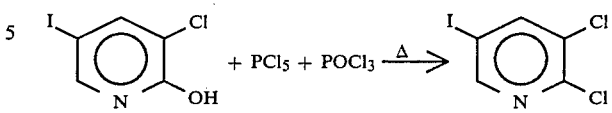

A 100 ml 3-necked round bottom flask, fitted with a condenser topped with a N₂ inlet, a mechanical stirrer and a thermometer, was charged with 17.2 g (0.0673 mole) of 3-chloro-2-hydroxy-5-iodopyridine, 14.85 g (0.0713 mole) of PCl₅, and 1 ml (1.68 g; 0.0109 mole) of POCl₃. The reaction mixture, containing solids, was slowly stirred and slowly heated to 130° C. The reaction mixture was stirred under N₂ for 5 hours after which it was cooled to room temperature and allowed to stand overnight. The reaction mixture was cautiously poured into crushed ice and allowed to stand for 1 hour. Methylene chloride (200 ml) was added to the reaction mixture to dissolve the solids present in it. The layers was separated and the organic phase was washed with dilute base, water and saturated NaCl. After drying over anhydrous MgSO₄ and filtration, the solvent was evaporated leaving 11.8 g of a yellow solid. The solid was recrystallized from methanol resulting in 6.60 g of solid that had spectral and physical properties identical to the product obtained in Example 1, STEP D.

The compound 3-chloro-5-iodo-2-pyridinol exists in equilibrium with its tautomer, 3-chloro-5-iodo-2-pyridone. Tautomerism is a phenomenon well known to those skilled in the art and the present invention contemplates both of the above tautomers. The tautomers can be characterized according to the following equilibrium equation:

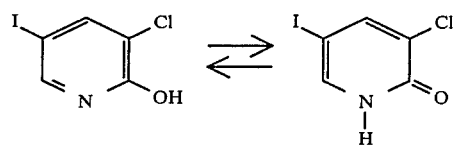

2,3-Dichloro-5-iodopyridine is useful as a chemical intermediate in the preparation of α-[4-(3-chloro-5-iodo-2-pyridyloxy)phenoxy propionic acid and derivatives thereof (salts, esters and amides), the preparation of which is well known to one skilled in the art employing procedures analogous to those described in the literature for preparing substituted pyridyloxyphenoxy propionic acids and derivatives thereof. Such procedures are described in the following references, all of which are incorporated herein by reference: EPO Patent Application No. 483; EPO Patent Application No. 82104766.9 (published Dec. 15, 1982); U.S. Pat. No. 4,046,553, U.S. Pat. No. 4,214,086; U.S. Pat. No. 4,275,212; U.S. Pat. No. 4,325,729; U.S. Pat. No. 4,266,063; U.K. Patent Specification No. 1,599,121; U.K. Patent Specification No. 1,599,122; and EPO 021613. In one method of preparation, 2,3-dichloro-5-iodopyridine is reacted with the dianion of hydroquinone to form 3-chloro-5-iodo-2-pyridyloxyphenol which is then reacted with an appropriate halopropionate to form the desired pyridyloxyphenoxy propionate. This reaction can be characterized as follows:

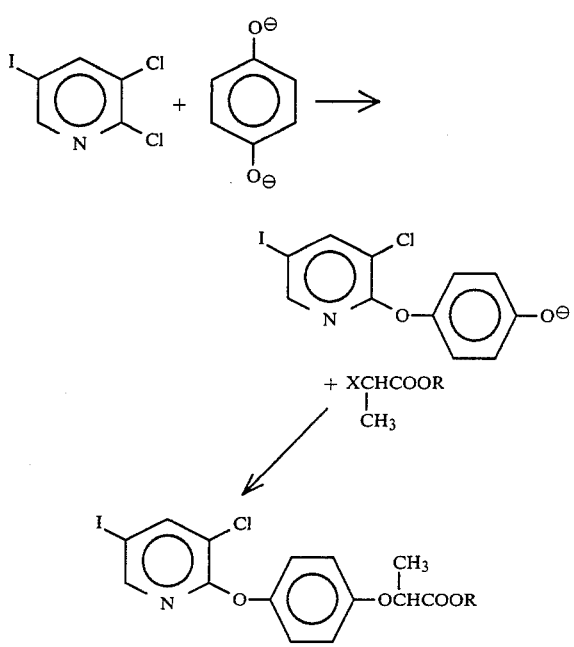

wherein

X represents Cl or Br, and

R represents H (the acid) or a moiety which forms an agriculturally acceptable salt, ester or amide of the acid, such as an alkaline earth metal cation, an alkali metal cation, a $C_1$–$C_{12}$ alkyl group or an amide group.

Another method of preparing the end product pyridyloxyphenoxy propionates is to react 2,3-dichloro-5-iodopyridine with a suitable anion of a 4-hydroxyphenoxy propionate. This reaction can be characterized as follows:

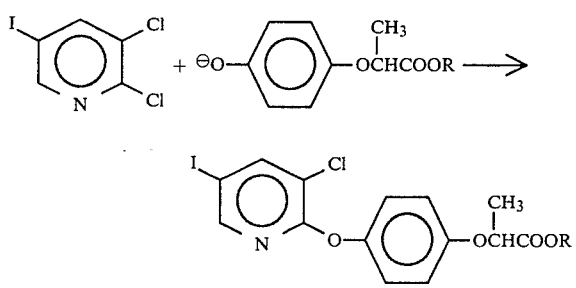

wherein R is as defined above.

I claim:

1. 2,3-Dichloro-5-iodopyridine.

2. A method of preparing 2,3-dichloro-5-iodopyridine which comprises:
   (a) reacting 5-bromo-2,3-dichloropyridine with an effective amount of an organolithium lithiating agent at a temperature below about −70° C. in an inert carrier medium to form 2,3-dichloro-5-lithiopyridine in situ, and then
   (b) adding to the reaction mixture an effective amount of $I_2$ at a teperature below about −70° C. whereby 2,3-dichloro-5-iodopyridine is formed.

3. The method of claim 2 wherein said lithiating agent is n-butyl lithium and said inert carrier medium is ethyl ether.

4. The method of claim 3 wherein the temperature is at or below about −78° C.

5. The method of claim 4 further comprising the steps of:
   (c) allowing the reaction mixture to warm to room temperature and
   (d) isolating 2,3-dichloro-5-iodopyridine from the reaction mixture.

6. 2,3-Dichloro-5-lithiopyridine.

7. A method of preparing 2,3-dichloro-5-lithiopyridine which comprises:
   (a) reacting 5-bromo-2,3-dichloropyridine with an effective amount of an organolithium lithiating agent at a temperature below about −70° C. in an inert carrier medium.

8. The method of claim 7 wherein the lithiating agent is n-butyl lithium.

9. The method of claim 8 wherein the temperature is at or below about −78° C.

10. A method of preparing 2,3-dichloro-5-iodopyridine which comprises:
    (a) reacting 3-chloro-5-iodo-2-pyridinol with an effective amount of a chlorinating agent selected from the group consisting of $COCl_2$, $Cl_2$, $PCl_5$, $POCl_3$, $SOCl_2$ or mixtures thereof at an elevated temperature under conditions sufficient to form 2,3-dichloro-5-iodopyridine.

11. The method of claim 10 wherein the chlorinating agent is a mixture of $PCl_5$ and $POCl_3$.

12. The method of claim 11 conducted at reflux.

13. The method of claim 12 further comprising the step of: isolating the 2,3-dichloro-5-iodopyridine from the reaction mixture.

14. 3-Chloro-5-iodo-2-pyridinol.

15. 3-Chloro-5-iodo-2-pyridinol in equilibrium with its tautomer 3-chloro-5-iodo-2-pyridone characterized by the equilibrium reaction:

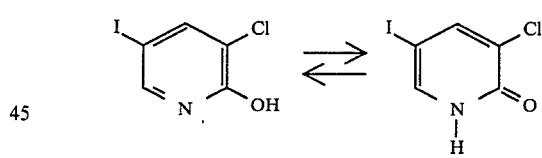

16. A method of preparing 3-chloro-5-iodo-2-pyridinol which comprises:
    (a) reacting 5-chloro-6-hydroxynicotinic acid with an effective amount of $I_2$ in an aqueous alkaline iodine solution under conditions to form 3-chloro-5-iodo-2-pyridinol.

17. The method of claim 16 wherein the reaction is conducted at a temperature of from about 40° C. to about 150° C.

18. The method of claim 17 wherein the temperature is about 100° C.

19. The method of claim 17 further comprising the steps of:
    (b) adjusting the pH of the reaction mixture to about 1 or less whereby 3-chloro-5-iodo-2-pyridinol forms as a precipitate and
    (c) isolating the precipitate.

20. The method of claim 19 wherein the pH is adjusted to about 1 or less by adding to the reaction mixture an effective amount of $SO_2$.

* * * * *